United States Patent
Casner et al.

(10) Patent No.: US 6,867,335 B2
(45) Date of Patent: Mar. 15, 2005

(54) UNCATALYSED ADDITION REACTIONS

(75) Inventors: Michael Casner, Pitman, NJ (US); Theodore Maurice Resnick, Bala Cynwyd, PA (US); Lee Jonathan Silverberg, Cherry Hill, NJ (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 10/478,940

(22) PCT Filed: May 9, 2002

(86) PCT No.: PCT/GB02/02160

§ 371 (c)(1),
(2), (4) Date: Jun. 7, 2004

(87) PCT Pub. No.: WO02/096846

PCT Pub. Date: Dec. 5, 2002

(65) Prior Publication Data

US 2004/0210076 A1 Oct. 21, 2004

(30) Foreign Application Priority Data

May 25, 2001 (GB) .............................................. 0112748

(51) Int. Cl.⁷ ......................... C07C 35/18; C07C 35/22; C07C 35/24; C07C 35/26; C07C 35/28

(52) U.S. Cl. ....................... 568/823; 568/816; 568/817; 568/819; 568/731; 568/732; 568/734; 568/743; 568/825

(58) Field of Search ................................. 568/823, 816, 568/817, 819, 825, 731, 732, 734, 743

(56) References Cited

U.S. PATENT DOCUMENTS

| | | | |
|---|---|---|---|
| 3,814,733 A | 6/1974 | Bledsoe et al. | |
| 4,025,516 A | 5/1977 | Razdan et al. | |
| 5,227,537 A | 7/1993 | Stoss et al. | |

OTHER PUBLICATIONS

Aïda L. Villa de P. et al., "Selective Epoxidation of Monoterpenes with Methyltrioxorhenium and $H_2O_2$," *Tetrahedron Letters*, vol. 39, 1998, pp. 8521–8524.

Leslie Crombie et al., "Acid–catalysed Terpenylations of Olivetol in the Synthesis of Cannabinoids," *J. Chem. Soc. Perkin Trans.*, vol. 1, 1998, pp. 1243–1250.

M. Bulliard et al., "Réaction de l'isopulégol d'alcools apparentés avec le chlorure de sulfuryle," *Bull. Soc. Fr.* vol. 128, 1991, pp. 222–231.

Benjamin C. Clark, Jr. et al., "Lewis Acid Rearrangement of 2,3–Epoxycarane. Formulation of a novel *m*–Menthenone," *J. Org. Chem.*, vol. 43, No. 3, pp. 519–520, 1982.

Kazushi Arata et al., "Isomerization of 2– and 3–Carene Oxides over Solid Acids and Bases," *J. Org. Chem.*, vol. 43, No. 9, 1978, pp. 1660–1664.

Raj K. Razdan et al., "Hashish. A Stereospecific Synthesis of (—)-$\Delta^{1}$-and (—)-$\Delta^{1(16)}$-Tetrahydrocannabinols," *Journal of the American Chemical Society*, vol. 19, No. 20, Oct. 7, 1970, pp. 6061–6062.

International Search Report dated Sep. 12, 2002, from International Application No. PCT/GB02/02160.

*Primary Examiner*—Elvis O. Price
(74) *Attorney, Agent, or Firm*—RatnerPrestia

(57) ABSTRACT

The present invention relates to process wherein (+)-2-carene epoxide is coupled with a compound X—Y that contains nucleophilic and electrophilic moieties, to produce a compound of formula (5). The reaction mixture consists essentially of a source of (+)-2-carene epoxide, compound X—Y, optionally an inert solvent and optionally a pH buffer. No acid catalyst is used in the process.

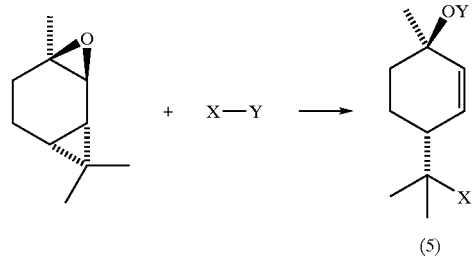

(5)

12 Claims, No Drawings

UNCATALYSED ADDITION REACTIONS

This application is the U.S. National Phase application of PCT International Application No. PCT/GB02/02160.

The present invention relates to novel synthetic processes wherein (+)-2-carene epoxide (1) is coupled with a variety of reagents in the absence of acid or base catalyst.

(+)-2-Carene epoxide (1) is a useful chiral intermediate that has been used as a precursor to tetrahydrocannabinoids. The acid-catalysed and base-catalysed rearrangements of (+)-2-carene epoxide (1) have been extensively studied. What these studies have in common is that mixtures of products are invariably obtained, and the yield of the desired compound is modest at best.

Bledsoe and coworkers found that by treating (+)-2-carene epoxide (1) with metatitanic acid, the rearranged product (+)-p-menthadienol (2) was obtained in 85% yield (U.S. Pat. No. 3,814,733). The present inventors have not achieved reproduction of Bledsoe's work. More typical is Bulliard's report of 44% yield of (2) when treating (1) with pyridinium para-toluenesulfonic acid (PPTS) in cyclohexane (Bull. Soc. Chim. Fr. 1991, 128, 222). Bledsoe also reports that treatment of (+)-2-carene epoxide (1) with 2% sulfuric acid in water gives a mixture containing 50% (+)-p-menth-2-ene-1,8-diol (3).

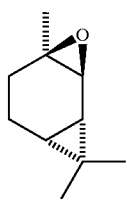

(1)

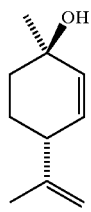

(2)

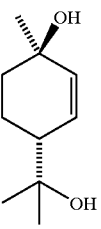

(3)

Arata, Bledsoe and Tanabe have published a study of the isomerisation of (+)-2-carene epoxide (1) over solid acids and bases (J. Org. Chem. 1978, 43, 1660). Clark has noted a different rearrangement of (1) using $ZnBr_2$ (J. Org. Chem. 1978, 43, 519). (+)-p-Menthadienol (2) and (+)-p-menth-2-ene-1,8-diol (3) are often major products in the catalysed rearrangements. The dienol (2) and the diol (3) have both been used to produce tetrahydrocannibinoids, particularly (−)-$\Delta^9$-Tetrahydrocannibinol ($\Delta^9$-THC). A synthetic route using the dienol (2) is disclosed by Razdan et al in U.S. Pat. No. 4,025,516, and a synthetic route using the diol (3) is disclosed by Stoss et al in U.S. Pat. No. 5,227,537.

$\Delta^9$-THC has also been synthesised directly by acid-catalysed reaction of (+)-2-carene epoxide (1) with olivetol (4), albeit in low yields. Razdan et al propose that this reaction is achieved via a ring-opened intermediate (scheme 1) (J. Amer. Chem. Soc. 1970, 6061). Cromble et al propose a mechanism involving a cyclopropylcarbinyl cation (scheme 2) (J. Chem. Soc. Perkin. Trans. 1, 1988, 1243).

Scheme 1.
Razdan mechanism

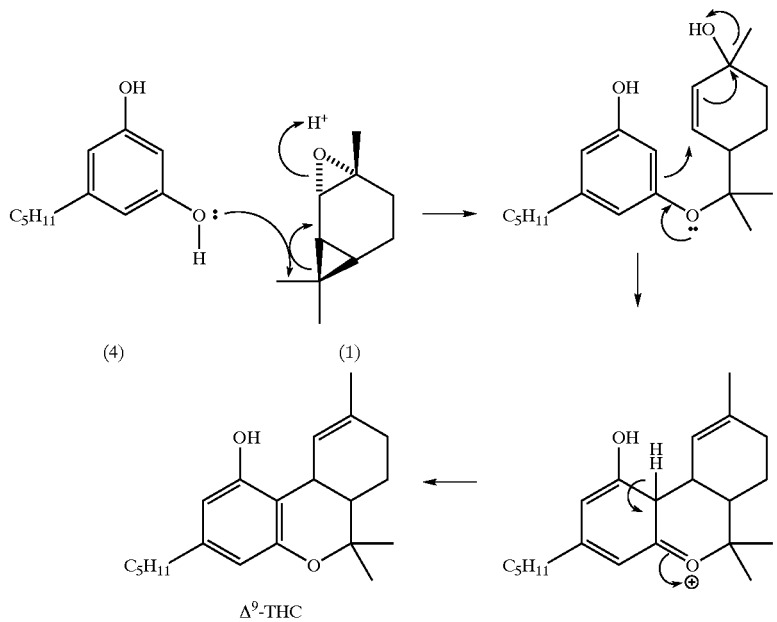

Scheme 2.
Crombie mechanism

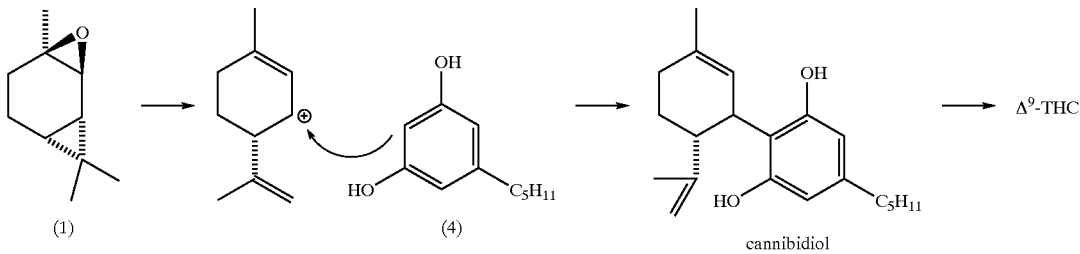

Mixtures of products and low yields generally result from the acid catalysed reactions of (+)-2-carene epoxide (1). This is probably due to the very high lability of the vicinal cyclopropyl-epoxy moiety to acid, which releases the strain energy of two three-membered rings and leads to the very stable cyclopropylcarbinyl cation. Base catalysed rearrangements similarly produce mixtures of products and low yields.

The present inventors have devised a synthetic route whereby (+)-2-carene epoxide (1) can be reacted cleanly and in high yield to produce useful, chiral products. The synthetic route requires neither acid nor base catalysts, as employed in prior art methods. Accordingly, the present invention provides a process for the producing a compound of general formula (5):

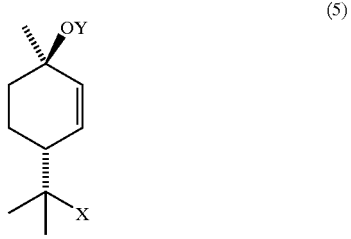

(5)

wherein X is a nucleophilic moiety and Y is an electrophilic moiety;
comprising the reaction of (+)-2-carene epoxide (1) with a compound of general formula X—Y wherein X and Y are as hereinbefore defined,

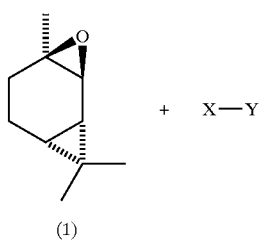

characterised in that the reaction mixture consists essentially of a source of (+)-2-carene epoxide (1), a compound of general formula X—Y, optionally an inert solvent and optionally a pH buffer.

In the context of this invention, the term "nucleophilic moiety" is used to describe a chemical group containing an electron rich centre. The term "electrophilic moiety" is used to describe a chemical group containing an electron deficient centre. Examples of X, a nucleophilic moiety, include OH and OR wherein R is alkyl, aryl, acyl or silyl. Examples of Y, an electrophilic moiety, include H and silyl.

Suitably the compound of general formula X—Y is water, an alcohol, a phenol, a carboxylic acid, a silanol, a silylated alcohol, a silylated phenol, a silylated carboxylic acid, a carbon acid, a thiol, a phosphite, or a phosphate. In a preferred embodiment of the invention, compound X—Y is water and the product of the process is (+)-p-menth-2-ene-1,8-diol (3):

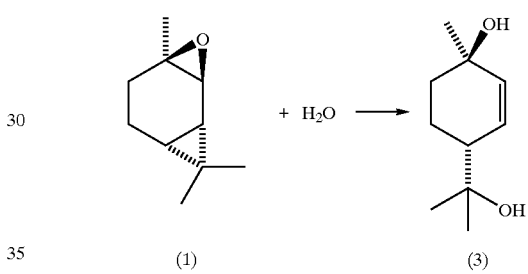

The direct reaction of (+)-2-carene epoxide (1) with water proceeds more cleanly than the prior art acid catalysed reactions of (+)-2-carene epoxide (1).

In a further embodiment of the invention, compound X—Y is an alcohol, a phenol or a carboxylic acid. In an especially preferred embodiment, compound X—Y is olivetol (4) and the product of the process is an ether (6):

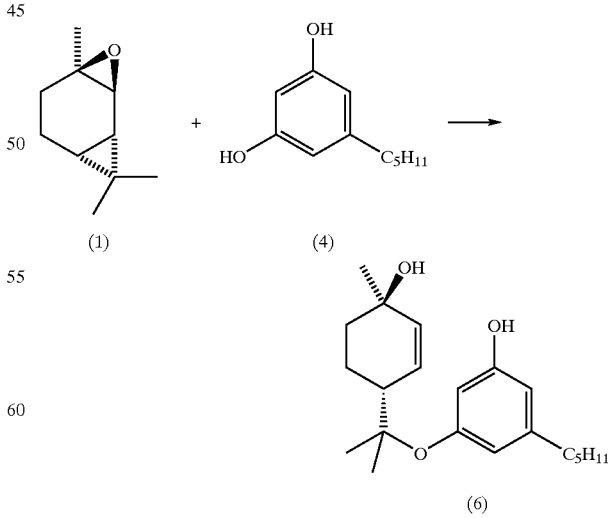

The ether (6) is proposed as an intermediate in the Razdan mechanism (scheme 1 above) but has not previously been isolated. Furthermore the Razdan mechanism is for an acid-catalysed reaction whereas there is no acid catalyst in the process of the present invention. The ether can be further converted to (−)-$\Delta^9$-Tetrahydrocannibinol ($\Delta^9$-THC) by a ring closure reaction. Reagents that will bring about the ring closure include $BF_3.(OEt)_2$ and t-BuOH. Therefore the present invention also provides a novel synthesis of $\Delta^9$-THC, comprising a first step wherein (+)-2-carene epoxide (1) is reacted with olivetol to produce an ether according to the process of the present invention, and a second step wherein the ether undergoes ring closure.

(+)-2-Carene epoxide (1) can be prepared by any of the methods known in the art. Suitable methods include epoxidation of (+)-2-carene (7) with perbenzoic acid, peracetic acid or m-CPBA. A preferred method is epoxidation using Jacobs' version of Sharpless' method (Tet. Lett. 1998, 39, 8521) wherein the reagents are $CH_3ReO_3$ catalyst, pyridine, hydrogen peroxide and $CH_2Cl_2$.

In the process of the present invention the reaction mixture contains a source of (+)-2-carene epoxide (1). The source of (+)-2-carene epoxide (1) may be distilled (+)-2-carene epoxide (1). The crude product of epoxidation can also be used as the source of (+)-2-carene epoxide (1). Another source of (+)-2-carene epoxide (1) is a mixture of (+)-2-carene epoxide (1) and (+)-3-carene epoxide. (+)-3-Carene (8) is an inexpensive component of turpentine. A catalytic isomerisation is generally used to produce (+)-2-carene (7). The isomerisation gives a 40:60 mixture of (+)-2-carene (7) and (+)-3-carene (8) and separation of the components is difficult because they have very similar boiling points. However, the inventors have found that if the mixture of isomers undergoes epoxidation, the mixture of epoxide isomers ((+)-2-carene epoxide (1) and (+)-3-carene epoxide) can be used as the source of (+)-2-carene epoxide in the present invention. This is because the (+)-3-carene epoxide does not undergo the addition reaction with compound X—Y and can be easily removed from the product of general formula (5). Therefore in a particular embodiment of the invention, the source of (+)-2-carene epoxide is a mixture of (+)-2-carene epoxide and (+)-3-carene epoxide.

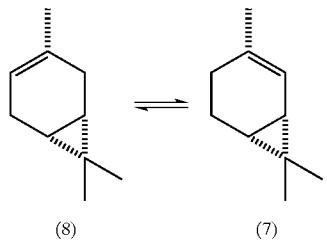

(8)        (7)

An inert solvent may be used in the process of the invention, but often compound X—Y will provide the only solvent needed (even though the reaction mixture may initially be heterogeneous). Suitable inert solvents include dichloromethane, 1,3-dioxolane and ethyl acetate.

A pH buffer is optionally included in the reaction mixture. The pH buffer is suitably employed when crude (+)-2-carene epoxide is used as the source of (+)-2-carene epoxide (1). Impurities present in the crude reagent can cause the pH to drop during the course of the reaction. A pH buffer can maintain the pH and the reaction proceeds more efficiently. A buffer is not required when distilled (+)-2-carene epoxide is used. When compound X—Y is water, a preferred pH range for the reaction is 5.7–5.9.

Suitably the process is carried out at room temperature or above, preferably between 10° C. to 150° C. The process is suitably carried out at atmospheric pressure.

The product of the process can be separated from the reaction mixture using methods known to those in the art. One suitable method is to use a separating funnel and extract the product using a solvent such as ethyl acetate or heptane. Methods of purification of the product include chromatography and, if the product is a solid, recrystallisation from organic solvents.

Preferably the reaction proceeds with a yield of at least 40%, more preferably with a yield of at least 50%.

The reaction suitably proceeds with retention of the stereochemistry at the two chiral centres.

The reactions of the present invention are significantly cleaner than similar reactions using acid catalysts. When acid catalysts are used, the cyclopropylcarbinyl cation is rapidly formed, which can rearrange to numerous products. We believe that when no acid catalyst is used, weak acids such as water and methanol react by a more concerted mechanism of the type proposed by Razdan (Scheme 1 above).

The present invention provides synthetic processes that may be used in industrial synthesis. (+)-p-Menth-2-ene-1,8-diol (3) is an important industrial precursor of $\Delta^9$-THC, and the present invention provides a clean, high-yielding synthesis from (+)-2-carene epoxide (1). Also, the present invention provides a process for the production of an ether (6), that may also be a useful intermediate in the industrial production of $\Delta^9$-THC.

The invention will now be described by way of example only:

General Experimental Details (+)-2-Carene (97%) was purchased from Aldrich Chemical Company (Milwaukee, Wis., USA). Samples of (−)-$\Delta^9$- and $\Delta^8$-THC were purchased from RBI/Sigma (Natick, Mass., USA). Anhydrous solvents were purchased from Aldrich Chemical Company. 1,3-Dioxolane was purchased from Ferro/Grant Chemical Co. (Cleveland, Ohio, USA). TLC plates (silica gel GF, 250 micron, 10×20 cm) were purchased from Analtech (Newark, Del., USA). TLCs were visualized under short wave UV, and then with $I_2$ or by spraying with ceric ammonium nitrate/sulfuric acid and heating. Column chromatography was carried out using TLC grade silica gel purchased from Aldrich Chemical Company. NMR spectra were obtained on a Bruker 300 MHz instrument.

Preparation of (+)-2-carene epoxide 900 mg methyl trioxorhenium was dissolved in 35% aqueous hydrogen peroxide and cooled to 0° C. internal in a 21, 3-necked flask. A solution was separately prepared from methylene chloride (0.71), (+)-2-carene (95.2 g, 0.698 mol), and pyridine (11.7 g). While stirring the aqueous solution vigorously, the methylene chloride solution was added over a two-hour period, keeping the exothermic reaction at 0–5° C. After three hours (when HPLC indicated disappearance of (+)-2-carene), the mixture was poured in to a separating funnel and the layers were separated. The organic layer was washed once with water (300 ml). The combined aqueous layers were extracted twice with methylene chloride (300 ml each). The organic layers were combined, dried with $Na_2SO_4$ and concentrated in vacuo (30° C., 30 mm) to give the product as a pale yellow mobile liquid (100 g). $^1H$ NMR was consistent with published reports. $R_f$ (5% EtOAc/hexane): 0.37.

Distillation of (+)-2-carene epoxide

Crude (+)-2-carene epoxide prepared as outlined above (9.76 g) was fractionally distilled under vacuum. The only major fraction was collected as a colourless liquid at 70.5–71.5° C. at 8 mm (8.01 g, 82.0% recovery). $^1$H NMR (CDCl$_3$): δ (ppm): 2.97 (d, 1H), 1.85 (quint., 1H), 1.63 (t, 2H), 1.53 (m, 1H), 1.22 (s, 3H), 1.02 (s, 3H), 1.00 (s, 3H), 0.61 (m, 1H). $^{13}$C NMR (CDCl$_3$): δ (ppm) 58.11, 57.85, 28.92, 27.14, 23.74, 21.94, 21.06, 20.69, 16.55, 16.39.

EXAMPLE 1

Reaction of crude (+)-2-carene epoxide with Water

Crude (+)-2-carene epoxide prepared as outlined above (60 g, 0.34 mol) was suspended in aqueous pH 5.8 buffer solution (1200 ml) and stirred vigorously. The internal temperature was warmed to 40° C. and held until starting material had disappeared by TLC and HPLC (3–6 hours). The reaction was cooled to room temperature, transferred to a separating funnel and washed once with heptane (300 ml). NaCl (180 g) was added to the aqueous layer and this was extracted with ethyl acetate (1×1l, 2×500 ml). The ethyl acetate extracts were combined, dried over Na$_2$SO$_4$, and concentrated in vacuo to give a white solid. Recrystallization from 5% EtOAc/heptane (300 ml) gave (+)-p-menth-2-ene-1,8-diol as flocculent white crystals (31.5 g, 51.3% from (+)-2-carene). Melting point: 112–113° C. (lit.114.5° C.). $^1$H NMR matched literature values. $^{13}$C NMR (CD$_3$OD): δ (ppm) 137.1, 129.0, 73.3, 70.2, 39.1, 28.8, 27.6, 26.0, 24.4. R$_f$ (50% EtOAc/hexane): 0.16. IR (KBr, cm$^{-1}$): 3383 (OH stretch), 3024 (alkene C-H stretch).

EXAMPLE 2

Epoxidation of (+)-2-carene and subsequent reaction with water 131 mg methyl trioxorhenium was dissolved in 30% aqueous hydrogen peroxide (23.6 ml) and cooled to 0° C. internal in a 2l, 3-necked flask. A solution was separately prepared from 1,3-dioxolane (100 ml), (+)-2-carene (13.6 g, 0.1 mol), and pyridine (12 ml). This was also cooled to 0° C. internal. While stirring the cold aqueous solution vigorously, the cold dioxolane solution was added over 70 minutes, keeping the exothermic reaction at 0–5° C. After three hours (when TLC indicated disappearance of (+)-2-carene), the mixture was poured in to a separating funnel and the layers were separated. Saturated NaCl solution (20 ml) was added to the aqueous layer and more separation occurred. The layers were separated again. The aqueous layer was extracted once more with dioxolane (10 ml). The organics were combined. Aqueous pH 5.8 buffer solution (304 ml) was added and stirred vigorously at room temperature until (+)-2-carene epoxide had disappeared by TLC and HPLC (4 hours). The reaction was transferred to a separating funnel and washed once with heptane (75 ml). NaCl (45 g) was added to the aqueous layer and this was extracted with ethyl acetate (3×125 ml, 1×100 ml). The ethyl acetate extracts were combined, dried over Na$_2$SO$_4$, and concentrated in vacuo to ~150 ml. 200 ml heptane was added and the solution was concentrated to ~150 ml. 5–10 ml of EtOAc was added to dissolve the solid. It was allowed to cool with stirring and then cooled to 0° C. The solid was collected by vacuum filtration and washed twice with cold 5% EtOAc/heptane. After drying under vacuum, 11.857 g of (+)-p-menth-2-ene-1,8-diol (69.8% yield from (+)-2-carene) was obtained. NMR showed some residual heptane. Elemental Analysis: 70.6% C, 10.6% H.

EXAMPLE 3

Isomerisation of (+)-3-carene followed by epoxidation and reaction with Water

A 100 ml roundbottom flask with a stir bar was dried with a heat gun, fitted with septa, and cooled under N$_2$. Potassium t-butoxide (10 g, 0.09 mol) was added. Anhydrous dimethylsulfoxide (25 ml) was added and stirred. (+)-3-Carene (13.6 g, 0.1 mol) was added. The mixture was heated to 100° C. and stirred overnight. After cooling, hexane (50 ml) was added and stirred. Water (50 ml) was added and stirred. The layers were separated. The aqueous layer was extracted with hexane (2×250 ml). The hexane layers were combined and washed with water, dried over Na$_2$SO$_4$, filtered, and concentrated in vacuo to oil (11 g). NMR analysis showed 58% (+)-3-carene and 42% (+)-2-carene.

100 mg methyl trioxorhenium was dissolved in 30% aqueous hydrogen peroxide (19 ml) and cooled to 0° C. internal in a 250 ml, 3-necked flask. A solution was separately prepared from 1,3-dioxolane (89 ml), the carene mixture (11 g), and pyridine (9 ml). This was also cooled to 0° C. internal. While stirring the cold aqueous solution vigorously, the cold dioxolane solution was added over 70 minutes, keeping the exothermic reaction at 0–5° C. After three hours, NaCl solution (20 ml) was added and the layers were separated. The aqueous layer was extracted once with dioxolane (25 ml). The organics were combined. Aqueous pH 5.8 buffer solution (275 ml) was added and stirred vigorously at room temperature for 1 hour, then 30° C. for 2.5 hours. The reaction was transferred to a separating funnel and washed once with heptane (100 ml). NaCl (43 g) was added to the aqueous layer and stirred for 30 min. The aqueous layer was extracted with ethyl acetate (1×100 ml, 2×250 ml). The ethyl acetate extracts were combined, dried over Na$_2$SO$_4$, and concentrated in vacuo to solid (2 g). The solid was dissolved in hot ethyl acetate. Heptane was added and the solution was allowed to cool with stirring and then cooled to 0° C. The solid was collected by vacuum filtration and washed with hexane. After drying under vacuum, 1.1 g (+)-p-menth-2-ene-diol (6.5% yield from (+)-3-carene) was obtained.

EXAMPLE 4

Reaction of distilled (+)-2-carene epoxide with water

Fractionally vacuum-distilled (+)-2-carene epoxide (1.00 g) was suspended in distilled water (30 ml). The internal temperature was warmed to 40° C. and held there for 6 hours. The reaction was cooled to room temperature, transferred to a separating funnel and washed once with heptane. The aqueous layer was extracted with ethyl acetate (7×75 ml). The ethyl acetate extracts were combined, washed with saturated NaCl solution, and concentrated in vacuo to give (+)-p-menth-2-ene-diol as a white crystalline powder (0.92 g, 82.3%).

EXAMPLE 5

Reaction of (+)-2-carene epoxide with methanol

A 50 ml roundbottom flask with a stir bar was oven-dried, fitted with septa, and cooled under N$_2$. Distilled (+)-2-carene epoxide (1.00 g) was added. Anhydrous methanol (40 ml) was added and stirred. A condenser was added and the solution was warmed to reflux for 28 hours. The solvent was removed in vacuo. The colourless oil was chromatographed on 30 g TLC mesh silica. 10% EtOAc/hexane eluted a UV active spot (25.5 mg), which appeared by NMR to be a methoxy diene. 30% EtOAc/hexane eluted a mixture of two spots (0.1836 g), which by NMR was partly dieneol. 40% EtOAc/hexane eluted a methyl ether corresponding to a compound of general formula (5) (0.8722 g, 72.1%). $^1$H NMR (CDCl$_3$): δ (ppm) 5.63 (s, 2H), 3.16 (s, 3H), 2.33–2.28 (m, 1H), 1.97–1.84 (m, 1H), 1.80–1.58 (m, 2H), 1.4–1.3 (m, 1H), 1.24 (s, 3H), 1.07 (s, 3H), 1.04 (s, 3H). $^{13}$C NMR (CDCl$_3$): δ (ppm) 136.63, 128.17, 76.57, 69.53, 48.77, 43.45, 38.45, 28.22, 22.95, 22.15, 21.98. Elemental Analysis: 67.12% C, 10.61% H. R$_f$ (40% EtOAc/hexane): 0.31. $[α]_D^{25}$=+37.1° (c=1.045, CHCl$_3$).

EXAMPLE 6

Reaction of (+)-2-carene epoxide with acetic acid

A 250 ml roundbottom flask with a stir bar was dried with a heat gun, fitted with septa, and cooled under N$_2$. Distilled (+)-2-carene epoxide (2.00 g) was added. Glacial acetic acid (80 ml) was added and stirred. TLC after one minute showed complete reaction. The acetic acid was removed under vacuum at 30° C. The colourless oil (2.355 g) was chromatographed on 50 g TLC mesh silica. 30–40% EtOAc/hexane eluted a monoacetate corresponding to a compound of general formula (5) (1.48 g, 53.2%). A minor product was also isolated (0.131 g, 6.55% yield) and the NMR matched that of (+)-p-menthadienol (compound 2). $^1$H and $^{13}$C NMR of the monoacetate matched literature values. Elemental Analysis: 62.35% C, 8.84% H. R$_f$ (50% EtOAc/hexane): 0.40. $[α]_D^{25}$=+32.1° (c=0.535, CHCl$_3$).

EXAMPLE 7

Reaction of (+)-2-carene epoxide with allyl alcohol

A 100 ml roundbottom flask with a stir bar was dried with a heat gun, fitted with septa, and cooled under N$_2$. Distilled (+)-2-carene epoxide (1.00 g) was added. Allyl alcohol (40 ml) was added and stirred. A condenser was added and the solution was warmed to 60° C. for one day, then 80° C. for one day, then reflux for three days. The solvent was removed in vacuo. The colourless oil was chromatographed on 30 g TLC mesh silica. 40% EtOAc/hexane eluted an allyl ether corresponding to a compound of general formula (5) (62 mg, 4.5%). $^1$H NMR (CDCl$_3$): δ (ppm) 5.87 (octet, 1H), 5.67 (dq, 2H), 5.28–5.21 (td, 1H), 5.11–5.06 (td, 1H), 3.88 (m, 2H), 1.92–1.86 (m, 1H), 1.85–1.7 (m, 1H), 1.7–1.6 (dt, 1H), 1.43 (m, 1H), 1.25 (s, 3H), 1.11 (s, 3H), 1.09 (s, 3H). $^{13}$C NMR (CDCl$_3$): δ (ppm) 135.99, 135.56, 128.40, 115.40, 7690, 69.63, 62.23, 44.08, 38.51, 28.22, 23.01, 22.77, 22.56. R$_f$ (20% EtOAc/hexane) 0.16.

EXAMPLE 8

Reaction of (+)-2-carene epoxide with ethylene glycol

A 100 ml roundbottom flask with a stir bar was dried with a heat gun, fitted with septa, and cooled under N$_2$. Distilled (+)-2-carene epoxide (1.00 g) was added. Ethylene glycol (40 ml) was added and stirred. A condenser was added and the solution was warmed to 60° C. for 2.5 hours. Water (40 ml) was added. The solution was poured in to a separating funnel and washed twice with hexane (20 ml each). The aqueous layer was then extracted with ethyl acetate (5×40 ml). The EtOAc extracts were combined and washed with saturated NaCl solution (20 ml), dried over Na$_2$SO$_4$, and filtered in vacuo. The colourless oil was chromatographed on 30 g TLC mesh silica. EtOAc eluted a glycol ether corresponding to a compound of general formula (5) (0.825 g, 58.6%). $^1$H NMR (CD$_3$OD): δ (ppm) 5.73–5.69 (td, 1H), 5.63–5.58 (td, 1H), 3.60 (t, 2H), 3.44 (t, 2.40–2.34 (m, 1H), 1.86–1.64 (m, 3H), 1.5–1.3 (m, 2H), 1.23 (s, 3H), 1.12 (s, 3H), 1.09 (s, 3H). $^{13}$C NMR (CD$_3$OD): δ (ppm) 136.91, 129.02, 78.02, 70.27, 63.69, 63.08, 45.38, 39.13, 28.80, 24.223, 23.34, 22.90, 21.04. Elemental Analysis: 64.49% C, 10.39% H. R$_f$(EtOAc): 0.38. $[α]_D^{25}$=+34.4° (c=0.956, CHCl$_3$).

EXAMPLE 9

Reaction of (+)-2-carene epoxide with t-butyldimethylsilanol

A 5 ml roundbottom flask with a stir bar was oven-dried, fitted with septa, and cooled under N$_2$. Distilled (+)-2-carene epoxide (100 mg) was added. t-Butyldimethylsilanol (1 ml) was added and stirred. A condenser was added and the solution was warmed to 125° C. for 20 hours, then 140° C. (reflux) for three days. After cooling, hexane was added and the solids were filtered off. The hexane solution was chromatographed on 5 g TLC mesh silica gel. A silyl ether corresponding to a compound of general formula (5) was obtained as a colourless oil (4.5 mg, 2.4%). $^1$H NMR (CDCl$_3$): δ (ppm) 5.79–5.74 (dd, 1H), 5.65–5.60 (dd, 1H), 2.2–2.1 (m, 1H), 1.9–1.8 (m, 2H), 1.7–1.3 (m, 2H), 1.26 (s, 3H), 1.19 (s, 3H), 1.13 (s, 3H), 0.85 (s, 9H), 0.08 (s, 6H). $^{13}$C NMR (CDCl$_3$): δ (ppm) 135.2, 129.2, 77.2, 75.2, 69.7, 48.3, 38.6, 29.7, 28.1, 27.7, 26.4, 25.8, 23.2, 18.1, 1.0, –0.06, –2.1. R$_f$ (20% EtOAc/hexane): 0.32.

EXAMPLE 10

Reaction of (+)-2-carene Epoxide with Olivetol

A 5 ml reactivial with a stir bar was oven-dried, capped and cooled under N$_2$. Distilled (+)-2-carene epoxide (1.00 g) was weighed in. Olivetol (1.77 g, 1.5 eq.) was added. The mixture was stirred at room temperature for 30 minutes, then warmed to 45° C. in an oil bath for 18 hours. The thick, light yellow oil was allowed to cool and then dissolved in ethyl acetate, evaporated onto silica gel, and chromatographed on 40 g TLC mesh silica gel. Fractions 29–35 contained clean olivetol ether corresponding to compound (6) (0.2373 g, 10.9%). Fractions 23–28 and 36–37 also contained some of the olivetol ether but at lower purity (0.3098 g, 14.2%). The olivetol ether was a colourless oil (total weight 0.5468 g, 25.0% yield). $^1$H NMR (CDCl$_3$): δ (ppm) 6.39 (dd, 2H), 6.33 (ds, 1H), 5.89 (d, 1H), 5.3 (d, 2H), 2.46 (t, 2H), 2.0–1.3 (m, ~11H), 1.29 (s, 3H), 1.19 (s, 3H), 1.16 (s, 3H), 0.86 (t, 3H). $^{13}$C NMR (CDCl$_3$): δ (ppm) 156.08, 155.88, 144.88, 135.70, 128.49, 116.60, 110.74, 108.60, 82.47, 70.00, 45.44, 38.36, 35.80, 31.40, 30.82, 28.22, 24.44, 23.32, 23.25, 22.48, 13.99. Elemental Analysis: 72.22% C, 10.34% H. R$_f$ (50% EtOAc/hexane): 0.45. $[α]_D^{25}$=+25.2° (c=0.159, CHCl$_3$).

EXAMPLE 11

Conversion of olivetol ether to Δ$^9$-THC

A 5 ml roundbottom flask with a stir bar was oven-dried, fitted with septa and cooled under N$_2$. The olivetol ether (6.4 mg) in anhydrous methylene chloride (0.8 ml) was added. Magnesium sulphate (30 mg) was added and stirred. The slurry was cooled to –40° C. BF$_3$.(OEt)$_2$ (5 µl) was added. TLC after five minutes showed three spots. The top spot cospotted with genuine Δ$^9$-THC.

EXAMPLE 12

Reaction of crude (+)-2-carene epoxide with olivetol in t-BuOH

A 5 ml roundbottom flask with a stir bar was oven-dried, fitted with septa, and cooled under N$_2$. Crude (+)-2-carene epoxide (100 mg) was added and the flask was evacuated and filled with $N_2$ three times. Olivetol (118 mg) was added. t-Butanol (1 ml) was added. A condenser was connected and the solution was warmed to 50° C. in an oil bath. TLC after two hours showed the olivetol ether forming. After three days, TLC showed the reaction had not changed. The temperature was turned up to reflux. After 10 minutes, TLC showed the olivetol ether had disappeared and two higher spots had formed. The top spot cospotted with genuine $\Delta^9$-THC. The solution was refluxed for one day, then allowed to cool. Chromatography on 5 g TLC mesh silica gel eluted three fractions of $\Delta^9$-THC (27.2 mg, 13.2% yield from (+)-2-carene epoxide) and five fractions of mixed $\Delta^9$- and $\Delta^8$-THC (15.0 mg, 7.3% yield). $^1$H NMR agreed with published reports and commercial sample.

EXAMPLE 13

Reaction of (+)-2-carene epoxide with trimethylsilyl methanol

A 10 ml roundbottom flask with a stir bar was oven-dried, fitted with septa, and cooled under $N_2$. Distilled (+)-2-carene epoxide (100 mg) was added. Trimethylsilyl methanol (2 ml) was added and stirred. A condenser was added and the solution was warmed to 100° C. for 30 hours. After cooling, the solvent was removed under vacuum. A yellowish oil was obtained (0.0929 g, 55.1% yield). NMR showed that the compound corresponded to general formula (5), but it was not pure. $^1$H NMR (CDCl$_3$): δ (ppm) 5.63 (m, 2H), 2.83 (s, 1H), 2.25 (m, 1H), 1.9–1.5 (m, 3H), 1.5–1.1 (m, 2H), 1.23 (s, 3H), 1.00 (s, 3H), 0.97 (s, 3H), −0.02 (s, 9H). $^{13}$C NMR (CDCl$_3$): δ (ppm) 135.11, 128.87, 110.83, 69.65, 52.30, 44.05, 42.49, 38.57, 28.89, 28.19, 27.74, 22.98, 21.90, 21.54, 21.09, 0.93, −3.19. R$_f$ (20% EtOAc/hexane): 0.52. $[\alpha]_D^{25}$=+17.0° (c=0.586, CHCl$_3$).

Table 1 summarises the reactants (compound X—Y) and the products (compound (5)) of the examples:

TABLE 1

| Example | Compound X–Y | Compound (5) |
| --- | --- | --- |
| 1, 2, 3, 4 | H$_2$O | |
| 5 | MeOH | |
| 6 | AcOH | |
| 7 | allyl alcohol | |
| 8 | HOCH$_2$CH$_2$OH | |
| 9 | t-butyldimethylsilanol | |
| 10, 12 | olivetol | |
| 13 | MeO—SiMe$_3$ | |

What is claimed is:

1. A process for producing a compound of general formula (5)

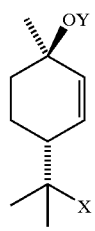
(5)

wherein X is a nucleophilic moiety and Y is an electrophilic moiety;

comprising reacting (+)-2-carene epoxide (1) with a compound of general formula X—Y in a reaction mixture, wherein X and Y are as hereinbefore defined,

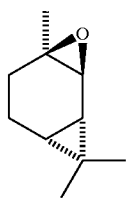
(1)

wherein the reaction mixture consists essentially of a source of (+)-2-carene epoxide (1), and the compound of general formula X—Y.

2. A process according to claim 1 wherein compound X—Y is selected from the group consisting of water, an alcohol, a phenol, a carboxylic acid, a silanol, a silylated alcohol, a silylated phenol, a silylated carboxylic acid, a carbon acid, a thiol, a phosphite, and a phosphate.

3. A process according to claim 2 wherein compound X—Y is water.

4. A process according to claim 2 wherein compound X—Y is selected from the group consisting of an alcohol, a phenol and a carboxylic acid.

5. A process according to claim 1 wherein compound X—Y is olivetol.

6. A process for producing a compound of general formula (5)

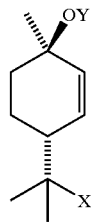
(5)

wherein X is a nucleophilic moiety and Y is an electrophilic moiety;

comprising reacting (+)-2-carene epoxide (1) with a compound of general formula X—Y in a reaction mixture, wherein X and Y are as hereinbefore defined,

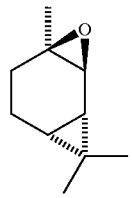
(1)

wherein the reaction mixture consists essentially of a source of (+)-2-carene epoxide (1), the compound of general formula X—Y, and one or both of an inert solvent and a pH buffer.

7. A process according to claim 6 wherein compound X—Y is selected from the group consisting of water, an alcohol, a phenol, a carboxylic acid, a silanol, a silylated alcohol, a silylated phenol, a silylated carboxylic acid, a carbon acid, a thiol, a phosphite, and a phosphate.

8. A process according to claim 7 wherein compound X—Y is water.

9. A process according to claim 7 wherein compound X—Y is selected from the group consisting of an alcohol, a phenol and a carboxylic acid.

10. A process according to claim 6 wherein compound X—Y is olivetol.

11. A process for the producing $(-)-\Delta^9$-Tetrahydrocannibinol comprising a first step and a second step which is a ring closure step, said first step comprising producing a compound of general formula (5)

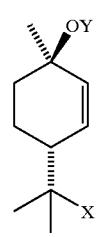
(5)

wherein X is a nucleophilic moiety and Y is an electrophilic moiety;

comprising reacting (+)-2-carene epoxide (1) with a compound of general formula X—Y in a reaction mixture, wherein X and Y are as hereinbefore defined,

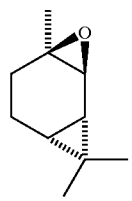
(1)

wherein the reaction mixture consists essentially of a source of (+)-2-carene epoxide (1), and a compound of general formula X—Y.

12. A process for the producing $(-)-\Delta^9$-Tetrahydrocannibinol comprising a first step and a second step which is a ring closure step, said first step comprising producing a compound of general formula (5)

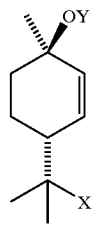

(5)

wherein X is a nucleophilic moiety and Y is an electrophilic moiety;

comprising reacting (+)-2-carene epoxide (1) with a compound of general formula X—Y in a

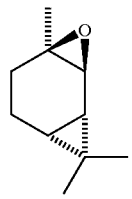

(1)

reaction mixture, wherein X and Y are as hereinbefore defined, wherein the reaction mixture consists essentially of a source of (+)-2-carene epoxide (1), and a compound of general formula X—Y, and one or both of an inert solvent and a pH buffer.

* * * * *